US00PP33020P2

(12) United States Plant Patent
Braeunig

(10) Patent No.: US PP33,020 P2
(45) Date of Patent: May 4, 2021

(54) ***ACHILLEA* PLANT NAMED 'FLORACHYE1'**

(50) Latin Name: *Achillea millefolium*
Varietal Denomination: FLORACHYE1

(71) Applicant: Florensis B.V., Hendrik-Ido-Ambacht (NL)

(72) Inventor: Tobias M. Braeunig, Quedlinburg (DE)

(73) Assignee: Florensis B.V., Hendrik-Ido-Ambacht (NL)

( * ) Notice: Subject to any disclaimer, the term of this patent is extended or adjusted under 35 U.S.C. 154(b) by 0 days.

(21) Appl. No.: 17/006,055

(22) Filed: Aug. 28, 2020

Related U.S. Application Data

(60) Provisional application No. 63/030,453, filed on May 27, 2020.

(51) Int. Cl.
*A01H 5/02* (2018.01)
*A01H 6/14* (2018.01)

(52) U.S. Cl.
USPC ..... Plt./263.1
CPC ..... *A01H 6/14* (2018.05)

(58) Field of Classification Search
USPC ..... Plt./263.1
CPC ..... A01H 6/14; A01H 5/02
See application file for complete search history.

*Primary Examiner* — Keith O. Robinson
(74) *Attorney, Agent, or Firm* — Audrey Charles

(57) ABSTRACT

A new and distinct cultivar of *Achillea* plant named 'FLORACHYE1', characterized by its medium yellow and red-orange colored inflorescences, medium green-colored foliage, low growth vigor and compact, upright-mounded growth habit, is disclosed.

1 Drawing Sheet

Latin name of genus and species of plant claimed: *Achillea millefolium.*
Variety denomination: 'FLORACHYE1'.

BACKGROUND OF THE INVENTION

The present invention relates to a new and distinct cultivar of *Achillea* plant botanically known as *Achillea millefolium* and hereinafter referred to by the cultivar name 'FLORACHYE1'.

The new cultivar originated in a controlled breeding program in Quedlinburg, Germany during May 2012. The objective of the breeding program was the development of *Achillea* cultivars having attractive flower coloration and a compact growth habit suitable for container plantings.

The new *Achillea* cultivar is the result of open-pollination. The female (seed) parent of the new cultivar is the proprietary *Achillea millefolium* breeding selection coded 10213-4, not patented, characterized by its medium orange-colored inflorescences, medium green-colored foliage, and vigorous, upright growth habit. The male (pollen) parent of the new cultivar is unknown. The new cultivar was selected as a single flowering plant within the progeny of the above stated open-pollination during July 2013 in a controlled environment in Quedlinburg, Germany.

Asexual reproduction of the new cultivar by terminal stem cuttings since July 2013 in Quedlinburg, Germany, Hendrik-Ido-Ambacht, The Netherlands, and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'FLORACHYE1' as a new and distinct cultivar of *Achillea* plant:

1. Medium yellow and red-orange colored inflorescences;
2. Medium green-colored foliage;
3. Low growth vigor; and
4. Compact, upright-mounded growth habit.

Plants of the new cultivar differ from plants of the female parent primarily in having a different inflorescence color and in having a more compact growth habit.

Of the many commercially available *Achillea* cultivars, the most similar in comparison to the new cultivar is Milly Rock Red 'FLORACHRE1', U.S. Plant Pat. No. 31,757. However, in comparison, plants of the new cultivar differ from plants of 'FLORACHRE1' in at least the following characteristics:

1. Plants of the new cultivar have medium yellow and red-orange colored inflorescences unlike the dark red-colored inflorescences of plants of 'FLORACHRE1'; and
2. Plants of the new cultivar have disc florets that are a lighter shade of yellow than plants of 'FLORACHRE1'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'FLORACHYE1'. The plants were approximately 4.5 months old. The plants were grown in 13 cm containers for 11 weeks outdoors in Hendrik-Ido-Ambacht, The Netherlands.

DETAILED BOTANICAL DESCRIPTION

Figure 1:
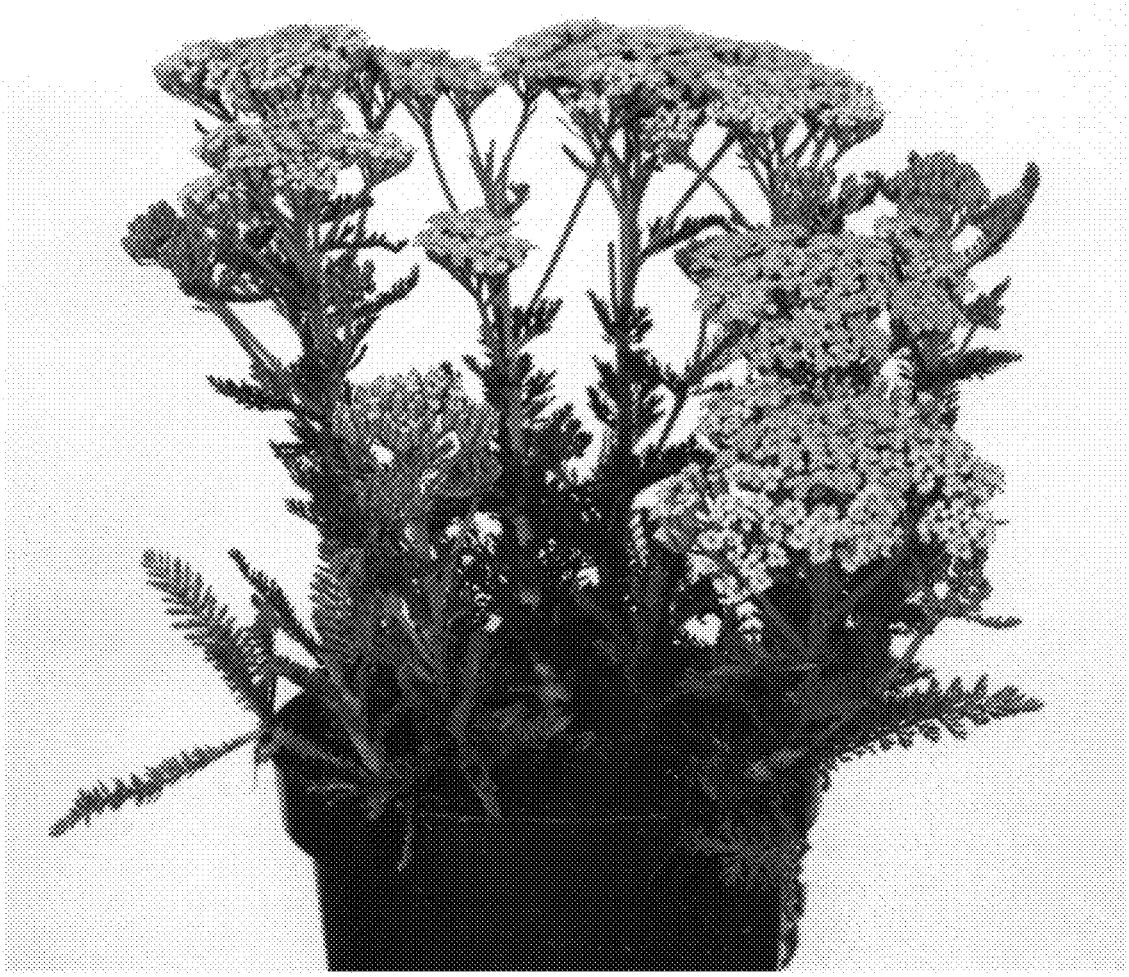
FIG. 1 illustrates a side view of the overall growth and flowering habit of 'FLORACHYE1'.
Figure 2:
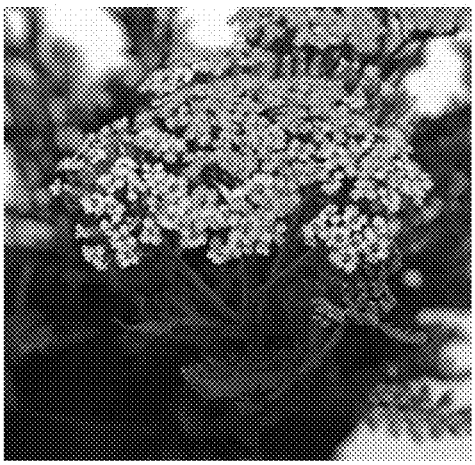
FIG. 2 illustrates a close-up view of an individual inflorescence of 'FLORACHYE1'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2020 under natural light conditions in Boskoop, The Netherlands.

The following descriptions and measurements describe approximately 4.5 month old plants produced from cuttings from stock plants and after transplant were grown outdoors in Hendrik-Ido-Ambacht, The Netherlands under conditions comparable to those used in commercial practice. The plants were grown in 13 cm pots utilizing a soilless growth medium for approximately 11 weeks. During this period the low temperatures ranged from 30.2° F. to 59.9° F. (−1° C. to 13.3° C.) and high temperatures ranged from 58.6° F. to 81.9° F. (14.8° C. to 27.7° C.). No supplemental lighting was provided. Measurements and numerical values represent averages of typical plants.

Botanical classification: *Achillea millefolium* 'FLORACHYE1'.

Propagation:

*Type cutting*.—Terminal stem.

*Time to initiate roots*.—Approximately 10 to 12 days.

*Time to produce a rooted cutting*.—Approximately 4 weeks.

*Root description*.—Moderately thick, fibrous.

*Rooting habit*.—Freely branching, moderately dense.

Plant description:

*Commercial crop time*.—Approximately 8 to 10 weeks from a rooted cutting to finish in a 10 cm pot.

*Growth habit and general appearance*.—Compact, upright-mounded.

*Size*.—Height from soil level to top of plant plane: Approximately 15.0 cm. Width: Approximately 24.2 cm.

*Branching habit*.—Freely branching, pinching enhances basal branching. Quantity of main branches per plant: Approximately 15.

*Branch*.—Strength: Strong. Length to base of cyme: Approximately 8.6 cm. Diameter: Approximately 3.0 mm. Length of central internode: Approximately 1.4 cm. Texture: Tomentose. Color of young stems: 145A. Color of mature stems: 138A.

Foliage description:

*General description*.—Quantity of leaves per main branch: Approximately 7. Fragrance: Faint. Form: Simple. Arrangement: Alternate.

*Leaves*.—Aspect: Acute angle to stem. Shape: Narrow oblanceolate. Margin: Very finely pinnately dissected giving a fern-like appearance. Apex: Acute. Base: Sessile, truncate. Venation pattern: Pinnate. Length of mature leaf: Approximately 9.4 cm. Width of mature leaf: Approximately 2.5 cm. Texture of upper surface: Sparsely pubescent. Texture of lower surface: Moderately pubescent. Color of upper surface of young foliage: 138A. Color of upper surface of mature foliage: 137B with midvein of 144B. Color of lower surface of young foliage: 138B. Color of lower surface of mature foliage: 137D with midvein of 147C.

Flowering description:

*Flowering habit*.—'FLORACHYE1' is freely flowering under outdoor growing conditions with substantially continuous blooming from late spring through summer.

*Lastingness of individual inflorescence on the plant*.—Approximately 10 to 14 days.

Inflorescence description:

*General description*.—Type: Rotate composite inflorescence form; inflorescences arranged in terminal or axillary compound cymes; cymes somewhat flat-topped; freely flowering; persistent. Aspect: Upward and slightly outward. Quantity per plant: Approximately 12. Cyme diameter: Approximately 7.1 cm. Cyme depth: Approximately 6.5 cm. Inflorescence diameter: Approximately 7.0 mm. Inflorescence depth: Approximately 5.0 mm. Fragrance: Slight.

*Peduncle*.—Strength: Strong. Aspect: Erect. Length: Approximately 4.7 cm. Diameter: Approximately 2.0 mm. Texture: Tomentose. Color of peduncle: 138A.

*Bud*.—Rate of opening: Generally takes 3 to 4 days for bud to progress from first color to fully open flower.

*Bud just before opening*.—Shape: Ovoid. Length: Approximately 5.0 mm. Diameter: Approximately 2.0 mm. Color: 138A with 150D and petals of 9D.

*Ray florets*.—Quantity per inflorescence: Approximately 4 to 5. Arrangement: In a single whorl. Aspect: Rotate. Shape: Orbicular on a narrow tube enclosing pistil. Margin: Entire. Apex: Three rounded tip to emarginate. Base: Attenuate. Length: Blade portion approximately 2.0 mm, tube portion approximately 3.5 mm. Width: Blade portion approximately 3.0 mm, tube portion approximately 0.5 mm. Texture of upper and lower surfaces: Glabrous. Texture of upper and lower surfaces: Glabrous. Color of upper surface when first open: 10A with a light overlay of 37A to 37B, concentrated at margins. Color of lower surface when first open: 10C narrowly margined with 37A. Color of upper surface when fully open: 10A with an overlay of 37A. Color of lower surface when fully open: 13D narrowly margined with 37A. Color of tube portion: 150C.

*Disc florets*.—Quantity per inflorescence: Approximately 14. Arrangement: Massed in center of inflorescence. Shape: Tubular. Margin: Entire. Apex: Five-acute tips. Base: Fused. Length: Approximately 5.0 mm. Diameter at apex: Approximately 1.5 mm. Diameter at base: Approximately 1.0 mm. Texture: Glabrous. Color when first open: 4C. Color when fully open: 4B to 4C, and base of 157A.

*Disc*.—Diameter: Approximately 3.0 mm. Depth: Approximately 1.0 mm.

*Receptacle*.—Shape: Dome. Height: Approximately 0.5 mm. Diameter at base: Approximately 2.5 mm. Color: 137B.

*Phyllaries*.—Quantity per inflorescence Approximately 15. Arrangement: In multiple whorls. Shape: Lanceolate to narrowly elliptic. Margin: Entire with papery edges. Apex: Acute. Base: Truncate. Length:

Approximately 2.0 mm to 3.5 mm. Width: Approximately 1.5 mm. Texture of upper surface: Glabrous. Texture of lower surface: Sparsely pubescent. Color of upper and lower surface: 138A margined with 157A.

*Reproductive organs.*—Androecium: Present on disc florets only. Stamen quantity: 5. Stamen length: Approximately 2.0 mm. Anther shape: Oblong. Anther length: Approximately 1.0 mm. Anther color: N199D. Pollen amount: Sparse. Pollen color: 14B. Gynoecium: Present on ray and disc florets. Pistil quantity: 1 per floret. Pistil length: Approximately 2.5 mm. Stigma shape: Bifid, occasionally trifid. Stigma length: Less than 1.0 mm. Stigma color: 9C. Style length: Approximately 2.0 mm. Style color: 145D. Ovary length: Approximately 0.5 mm. Ovary color: 157A.

Seed and fruit production: Neither seed nor fruit production has been observed.

Disease and pest resistance: Resistance to pathogens and pests common to *Achillea* has not been observed.

What is claimed is:

1. A new and distinct cultivar of *Achillea* plant named 'FLORACHYE1', substantially as herein illustrated and described.

* * * * *